(12) United States Patent
Denham et al.

(10) Patent No.: US 12,023,014 B2
(45) Date of Patent: Jul. 2, 2024

(54) RATCHETING HANDLE FOR MEDICAL INSTRUMENT

(71) Applicant: Nextremity Solutions, Inc., Warsaw, IN (US)

(72) Inventors: Gregory Denham, Warsaw, IN (US); Joseph Whitley, Leesburg, IN (US); Ryan Schlotterback, Fort Wayne, IN (US)

(73) Assignee: NEXTREMITY SOLUTIONS, INC., Warsaw, IN (US)

( * ) Notice: Subject to any disclaimer, the term of this patent is extended or adjusted under 35 U.S.C. 154(b) by 709 days.

(21) Appl. No.: 17/210,609

(22) Filed: Mar. 24, 2021

(65) Prior Publication Data

US 2021/0315555 A1    Oct. 14, 2021

Related U.S. Application Data

(60) Provisional application No. 63/007,993, filed on Apr. 10, 2020.

(51) Int. Cl.
*A61B 17/00* (2006.01)

(52) U.S. Cl.
CPC .... *A61B 17/00* (2013.01); *A61B 2017/00407* (2013.01); *A61B 2017/0046* (2013.01); *A61B 2017/00477* (2013.01)

(58) Field of Classification Search
CPC .......... A61B 17/00; A61B 2017/00407; A61B 2017/0046; A61B 2017/00477; A61B 17/8875; A61B 2017/00398; A61B 17/162; B25B 13/46; B25B 15/04
See application file for complete search history.

(56) References Cited

U.S. PATENT DOCUMENTS

| | | | |
|---|---|---|---|
| 1,829,421 A | 10/1931 | Roe | |
| 3,209,802 A * | 10/1965 | Human | B25B 15/06 81/58.4 |
| 3,651,718 A | 3/1972 | Thomasian | |
| 4,224,969 A * | 9/1980 | Plessner | B25F 3/00 403/287 |
| 4,413,937 A * | 11/1983 | Gutsche | B25F 3/00 408/239 R |
| 4,777,852 A | 10/1988 | Herman et al. | |
| 5,255,576 A * | 10/1993 | Keith | B25B 13/12 81/125 |
| 5,368,480 A | 11/1994 | Balfour et al. | |

(Continued)

FOREIGN PATENT DOCUMENTS

| | | |
|---|---|---|
| WO | 2019005665 A1 | 1/2019 |
| WO | 2019006563 A1 | 1/2019 |

(Continued)

*Primary Examiner* — David Hamaoui
*Assistant Examiner* — Rumaisa Rashid Baig
(74) *Attorney, Agent, or Firm* — Heslin Rothenberg Farley & Mesiti P.C.

(57) ABSTRACT

A ratcheting handle for a medical instrument is provided that includes a ratchet shifter, a tool connector, a ratchet coupler, and a rear power housing. The handle provides clockwise and counterclockwise ratcheting. In one aspect, the ratcheting handle may include a drive shaft removeably connected to a power tool or, alternatively, to a handle grip for manual manipulation.

10 Claims, 15 Drawing Sheets

(56) References Cited

U.S. PATENT DOCUMENTS

| | | | |
|---|---|---|---|
| 5,673,594 A * | 10/1997 | Huang | B62M 25/04 |
| | | | 74/489 |
| 5,685,204 A | 11/1997 | Braun | |
| 5,746,298 A | 5/1998 | Krivec et al. | |
| 6,070,501 A * | 6/2000 | Braun | B25B 13/463 |
| | | | 81/62 |
| 6,076,432 A * | 6/2000 | Chang | B25B 15/04 |
| | | | 81/439 |
| 6,199,872 B1 * | 3/2001 | Hasan | B25B 23/0042 |
| | | | 279/155 |
| 6,439,086 B1 | 8/2002 | Bahr | |
| 6,817,458 B1 | 11/2004 | Gauthier | |
| 6,948,605 B1 | 9/2005 | Gauthier | |
| 7,156,216 B2 | 1/2007 | Gauthier | |
| 7,213,491 B1 * | 5/2007 | Thompson | B25B 13/466 |
| | | | 81/58.3 |
| 7,243,580 B2 | 7/2007 | Frazee | |
| 7,272,999 B2 | 9/2007 | Cutler et al. | |
| 7,413,065 B2 | 8/2008 | Gauthier | |
| 7,762,161 B2 | 7/2010 | Lai | |
| 7,942,253 B2 | 5/2011 | Schneeman et al. | |
| 7,946,198 B2 * | 5/2011 | Gui | B25B 15/04 |
| | | | 81/58.1 |
| 8,033,200 B2 | 10/2011 | Johnson et al. | |
| 8,065,940 B2 | 11/2011 | Wilson et al. | |
| 8,096,214 B2 | 1/2012 | Gao | |
| 8,136,431 B2 | 3/2012 | Wengreen | |
| 8,276,487 B2 | 10/2012 | Wengreen et al. | |
| 8,113,095 B2 | 11/2012 | Gao | |
| 8,336,428 B2 | 12/2012 | Johnson et al. | |
| 8,430,868 B2 | 4/2013 | Edgell et al. | |
| 8,490,525 B2 | 7/2013 | Wilson et al. | |
| 8,757,033 B2 | 6/2014 | Wagic | |
| 8,757,035 B2 | 6/2014 | Kerboul et al. | |
| 8,790,327 B2 | 7/2014 | Takemoto | |
| 8,875,602 B2 | 11/2014 | Wengreen et al. | |
| 8,893,589 B2 | 11/2014 | Kibby | |
| 9,107,721 B2 | 8/2015 | Plotkin | |
| 9,156,145 B2 | 10/2015 | Wang | |
| 9,421,675 B2 | 8/2016 | Yu | |
| 9,504,528 B2 | 11/2016 | Ivinson et al. | |
| 9,555,526 B1 | 1/2017 | Gauthier et al. | |
| 9,572,617 B1 | 2/2017 | Prado et al. | |
| 9,643,298 B2 * | 5/2017 | Wang | B25B 17/00 |
| 9,668,797 B2 | 6/2017 | Ivinson et al. | |
| 9,693,814 B2 | 7/2017 | Schaller et al. | |
| 9,695,882 B2 | 7/2017 | Jakoubek | |
| 9,757,175 B2 | 9/2017 | Plotkin | |
| 9,770,813 B2 | 9/2017 | Wang | |
| 9,855,088 B2 | 1/2018 | Stank et al. | |
| 9,868,194 B2 | 1/2018 | Ivinson et al. | |
| 9,969,066 B2 | 5/2018 | Li | |
| 9,987,066 B2 | 6/2018 | Stad et al. | |
| 10,034,701 B2 | 7/2018 | Adamiec | |
| 10,118,278 B2 | 11/2018 | Thompson et al. | |
| 10,189,150 B2 | 1/2019 | Healey et al. | |
| 10,194,988 B2 | 2/2019 | Schaller et al. | |
| 10,195,724 B2 | 2/2019 | Nino et al. | |
| 10,213,270 B2 | 2/2019 | Cutler | |
| 10,322,497 B2 | 6/2019 | Thompson et al. | |
| 10,335,930 B2 | 7/2019 | Cutler | |
| 10,413,345 B2 | 9/2019 | Plotkin | |
| 10,434,631 B2 | 10/2019 | Johnson et al. | |
| 10,463,449 B2 | 11/2019 | Martin | |
| 10,588,640 B2 | 3/2020 | Steinhauser et al. | |
| 10,624,653 B2 | 4/2020 | Chien et al. | |
| 2006/0248988 A1 * | 11/2006 | Bennett | B25B 15/04 |
| | | | 81/62 |
| 2007/0062340 A1 * | 3/2007 | Li | B25B 15/04 |
| | | | 81/63.1 |
| 2007/0290458 A1 * | 12/2007 | Chuang | B25F 3/00 |
| | | | 279/143 |
| 2008/0092695 A1 * | 4/2008 | Hernandez | B25B 13/463 |
| | | | 81/62 |
| 2008/0308376 A1 | 12/2008 | Gauthier | |
| 2009/0133980 A1 | 5/2009 | Swaim et al. | |
| 2009/0192501 A1 | 7/2009 | Miletto et al. | |
| 2009/0228051 A1 * | 9/2009 | Kolb | A61B 17/7032 |
| | | | 606/301 |
| 2009/0234365 A1 | 9/2009 | Gross | |
| 2010/0107829 A1 | 5/2010 | Zimmerman et al. | |
| 2010/0116097 A1 | 5/2010 | Xu | |
| 2010/0154600 A1 * | 6/2010 | Gui | B25B 15/04 |
| | | | 81/436 |
| 2010/0298838 A1 * | 11/2010 | Walters | E04G 1/24 |
| | | | 606/104 |
| 2012/0291599 A1 | 11/2012 | Cutler | |
| 2013/0205853 A1 * | 8/2013 | Adomavicius | E04G 5/005 |
| | | | 72/392 |
| 2014/0260816 A1 * | 9/2014 | Budleski | B25B 17/00 |
| | | | 81/57.39 |
| 2015/0066056 A1 * | 3/2015 | Cabrera Aquino | |
| | | | A61B 17/12013 |
| | | | 606/140 |
| 2015/0096413 A1 * | 4/2015 | Knight | B25B 21/004 |
| | | | 81/57.13 |
| 2015/0101464 A1 | 4/2015 | Cutler | |
| 2015/0101465 A1 | 4/2015 | Cutler | |
| 2015/0209942 A1 | 7/2015 | Hongquan | |
| 2015/0328750 A1 | 11/2015 | Thompson et al. | |
| 2015/0342693 A1 | 12/2015 | Ivinson et al. | |
| 2016/0151895 A1 * | 6/2016 | Markiewicz | B25B 23/141 |
| | | | 81/474 |
| 2017/0079706 A1 | 3/2017 | Rinner | |
| 2017/0105813 A1 | 4/2017 | Rash et al. | |
| 2017/0265921 A1 | 9/2017 | Faccioli et al. | |
| 2017/0314711 A1 | 11/2017 | Helstern | |
| 2017/0365949 A1 | 12/2017 | Montena et al. | |
| 2018/0206856 A1 | 7/2018 | Hogerle et al. | |
| 2018/0222021 A1 | 8/2018 | Plehn-Citrone | |
| 2018/0256234 A1 | 9/2018 | Stad et al. | |
| 2018/0369998 A1 | 12/2018 | Cutler | |
| 2019/0000523 A1 | 1/2019 | Goodwin, Jr. et al. | |
| 2019/0022831 A1 | 1/2019 | Buchanan | |
| 2019/0022833 A1 | 1/2019 | Macke et al. | |
| 2019/0125421 A1 | 5/2019 | Smith et al. | |
| 2019/0126449 A1 | 5/2019 | Poonawalla et al. | |
| 2019/0126450 A1 | 5/2019 | Gauthier et al. | |
| 2020/0008854 A1 | 1/2020 | Plotkin | |
| 2020/0030948 A1 * | 1/2020 | Meehan | B25B 15/06 |
| 2020/0384615 A1 * | 12/2020 | Ruetschi | B25B 23/1427 |

FOREIGN PATENT DOCUMENTS

| | | | |
|---|---|---|---|
| WO | 2019089348 A1 | 5/2019 | |
| WO | 2019089931 A1 | 5/2019 | |
| WO | 2019157380 A1 | 8/2019 | |

* cited by examiner

RATCHETING HANDLE FOR MEDICAL INSTRUMENT

BACKGROUND OF THE INVENTION

Technical Field

The present invention generally relates to handles for a surgical instrument or device, and more particularly, to quick disconnect handles for a surgical instrument or device that provides clockwise and counter-clockwise ratcheting.

Background Information

Current disposable handles on the market tend to be very expensive and cumbersome to use for a surgeon during operation. With, for example, a normal screwdriver device, a surgeon would have to seat the driver, turn the screw then remove the driver and reseat it before turning again. This process slows down an operation and could cause mistakes and other problems during reseating of the device.

Thus, a need exists for a handle for a surgical instrument or device that does not, for example, require constant reseating during use.

SUMMARY OF THE INVENTION

Briefly, the handle constructed in accordance with one or more aspects of the present invention satisfies the need for providing clockwise and counterclockwise ratcheting for a quick disconnect handle for a surgical instrument or device. Two way ratcheting makes installation easier overall. With a ratchet mechanism constructed in accordance with one or more aspects of the present invention, a surgeon will only need to seat the driver once and then can spin back freely in both directions (e.g. inserting and removing a screw). This takes two steps out of the installation process making it significantly faster.

In one aspect of the present invention, an apparatus for releasably holding a surgical tool is provided. The apparatus comprises a ratchet shifter, a tool connector, a ratchet coupler and a rear power housing. The ratchet shifter includes a proximal end, a distal end and a body defining a through-hole. The tool connector includes a longitudinal axis, a proximal end and a distal end. The tool connector further includes a tool engagement body extending from the proximal end and a mounting post extending longitudinally along the longitudinal axis from the tool engagement body to the distal end. The tool engagement body includes a tool engagement opening at the proximal end communicating with a longitudinal bore extending through at least a portion of the tool engagement body along the longitudinal axis. The longitudinal bore is configured to releasably couple the surgical tool. The ratchet shifter telescopically receives the tool connector and is slidably moveable between a first position and a second position.

The ratchet coupler includes a body defining a through-hole and an outer surface. The mounting post of the tool connector passes through the through hole of the cylindrical body. The mounting post is slidably coupled to the ratchet coupler. The distal end of the ratchet shifter is coupled to the ratchet coupler. The outer surface of the ratchet coupler includes a first forward portion and a second rear portion. The first forward portion includes a plurality of fingers extending radially outward from the outer surface. The second rear portion includes a plurality of fingers extending radially outward from the outer surface.

The rear power housing is rotatably coupled to the mounting post of the tool connector at the distal end. The rear power housing includes a longitudinal axis, a body and a drive shaft extending longitudinally along the longitudinal axis from the body. The body includes a cavity defining an inner surface. The inner surface comprises a forward circumferential surface, a neutral circumferential surface and a rear circumferential surface. The forward circumferential surface includes a plurality of teeth projecting radially inward from the inner surface. The rear circumferential surface includes a plurality of teeth projecting radially inward from the inner surface.

In the first position, the plurality of fingers of the first forward portion of the ratchet coupler engage the plurality of teeth on the forward circumferential surface to allow ratcheting in a first direction and maximum torque in a second direction and the plurality of teeth of the second rear portion engage the neutral circumferential surface. In the second position, the plurality of fingers of the second rear portion of the ratchet coupler engage the plurality of teeth on the rear circumferential surface to allow ratcheting in the second direction and maximum torque in the first direction and the plurality of teeth of the first forward portion engage the neutral circumferential surface.

In another aspect, the rear power housing of the apparatus for releasably holding a surgical tool is removeably attachable to a handle grip.

These, and other objects, features and advantages of this invention will become apparent from the following detailed description of the various aspects of the invention taken in conjunction with the accompanying drawings.

BRIEF DESCRIPTION OF THE DRAWINGS

The present invention will be understood more fully from the detailed description given hereinafter and from the accompanying drawings of the certain embodiments of the present invention, which, however, should not be taken to limit the invention, but are for explanation, illustration and understanding only.

DETAILED DESCRIPTION OF THE INVENTION

Figure 1A:
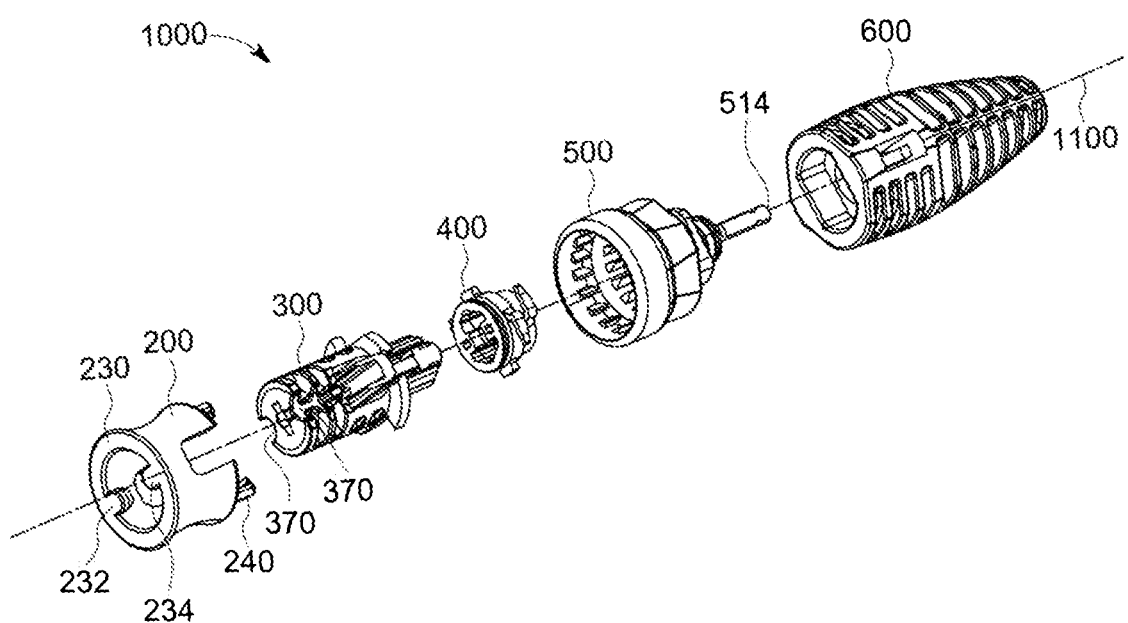
FIG. 1A depicts an exploded perspective view of a handle with an optional handle grip constructed in accordance with one or more aspects of the present invention.

The present invention will be discussed hereinafter in detail in terms of various exemplary embodiments according to the present invention with reference to the accompanying drawings. In the following detailed description, numerous specific details are set forth in order to provide a thorough understanding of the present invention. It will be obvious, however, to those skilled in the art that the present invention may be practiced without some of these specific details. In other instances, well-known structures are not shown in detail in order to avoid unnecessary obscuring of the present invention.

Thus, all implementations described below are exemplary implementations provided to enable persons skilled in the art to make or use the embodiments of the disclosure and are not intended to limit the scope of the disclosure, which is defined by the claims. As used herein, the word "exemplary" or "illustrative" or "example", and derivatives thereof, means "serving as an example, instance, or illustration." Any implementation described herein as "exemplary" or "illustrative" or "example", and derivatives thereof, is not necessarily and should not be construed as preferred or advantageous over other implementations. Moreover, in the present description, the terms "upper", "lower", "left", "rear", "right", "front", "vertical", "horizontal", and derivatives thereof shall relate to the invention as oriented in FIG. 1A.

Furthermore, there is no intention to be bound by any expressed or implied theory presented in the preceding technical field, background, brief summary or the following detailed description. It is also understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise. While this invention is satisfied by embodiments in many different forms, there is shown in the drawings, and will herein be described in detail, one or more embodiments of the present invention with the understanding that the present disclosure is to be considered as exemplary of the principles and aspects of the invention and is not intended to limit the invention to the embodiments illustrated. The scope of the invention will be pointed out in the appended claims.

In short, a handle constructed in accordance with one or more aspects of the present invention provides a quick disconnect handle for use with a surgical instrument, such as, for example, a drill bit or screwdriver, that provides clockwise and counterclockwise ratcheting. The handle may be operated manually by an optional removable handle grip or by power with a power instrument removably attached.

Figure 1B:
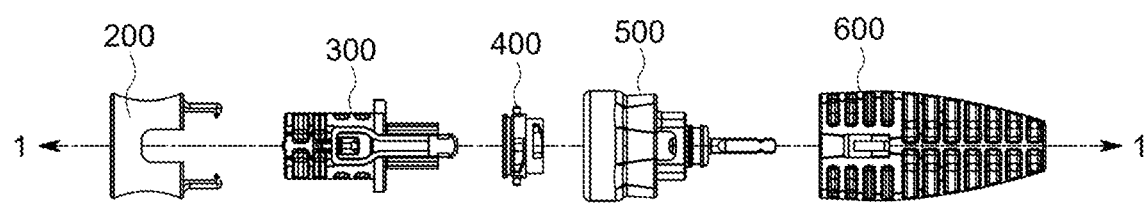
FIG. 1B depicts a side view of the handle shown in FIG. 1A.
Figure 1C:
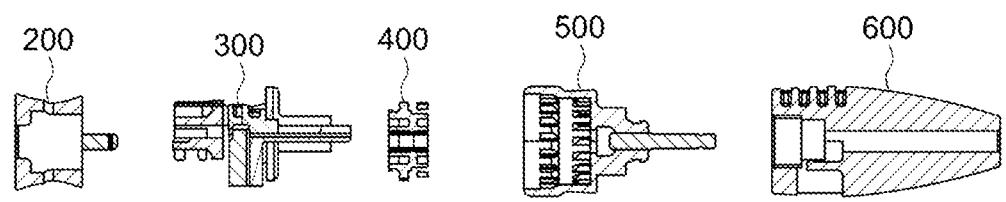
FIG. 1C depicts a cross-sectional view of the handle shown in FIG. 1B, rotated clockwise ninety degrees and taken along the plane 1-1.

Referring now to FIGS. 1A-1C, there are shown various exploded views of a handle 1000 constructed in accordance with one or more aspect of the present invention. As illustrated in FIGS. 1A and 1B, handle 1000 may include a ratchet shifter 200, a tool connector 300, a ratchet coupler 400, a rear power housing 500 and an optional handle grip 600. Each of ratchet shifter 200, tool connector 300, a ratchet coupler 400, a rear power housing 500 and an optional handle grip 600 share a common longitudinal or rotational axis 1100. Handle is configured to couple to a medical instrument or tool such as, for example, a screw driver or drill. In one example, a screw driver or drill is positively and removably grasped or coupled to a coupling mechanism provided at a proximal end 314 of tool connector 300 of handle 1000. The coupling mechanism, which will be described in more detail below, is configured to transfer the torque applied to handle 1000 to the medical instrument or tool.

Ratchet shifter 200, tool connector 300, ratchet coupler 400 and rear power housing 500 are assembled and not separable during use. The assembly of ratchet shifter 200, tool connector 300, ratchet coupler 400 and rear power housing 500 may readily and removably couple or attach, at distal end 514 of rear power housing 500, to a power instrument or tool, such as, for example, a cordless power drill. Instead of attaching to a power instrument or tool, the assembly of ratchet shifter 200, tool connector 300, ratchet coupler 400 and rear power housing 500 may also readily and removably couple or attach to an optional handle grip 600 for manual operation such as, for example, inserting a screw manually. Handle grip 600 may be removed or added by an end user to transition between power and manual application of torsion applied to handle 1000.

Figure 2A:
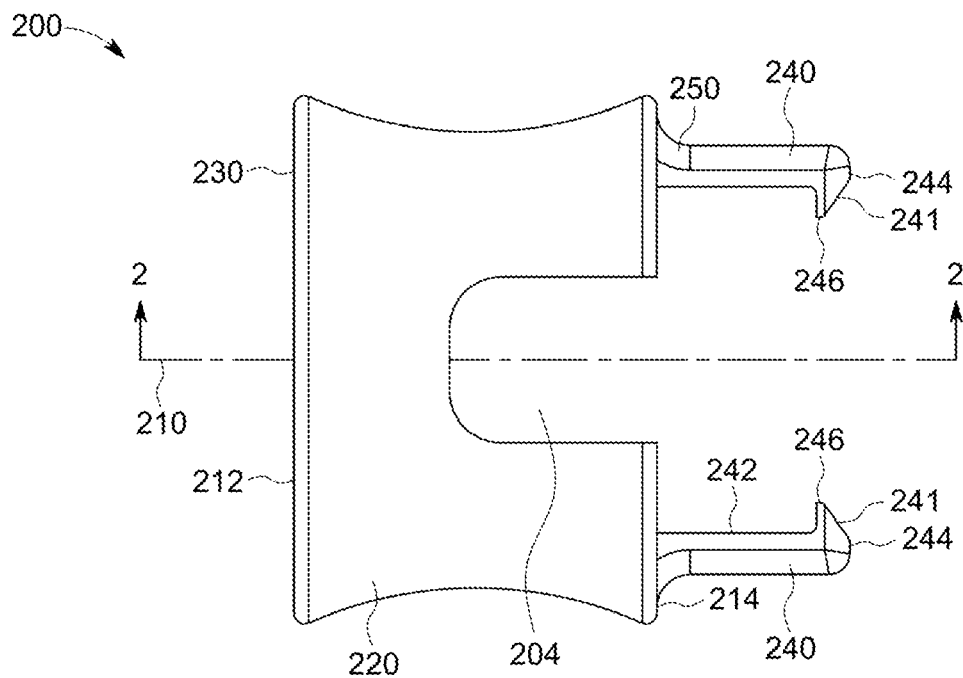
FIG. 2A depicts a side view of a ratchet shifter for a handle constructed in accordance with one or more aspects of the present invention.
Figure 2B:
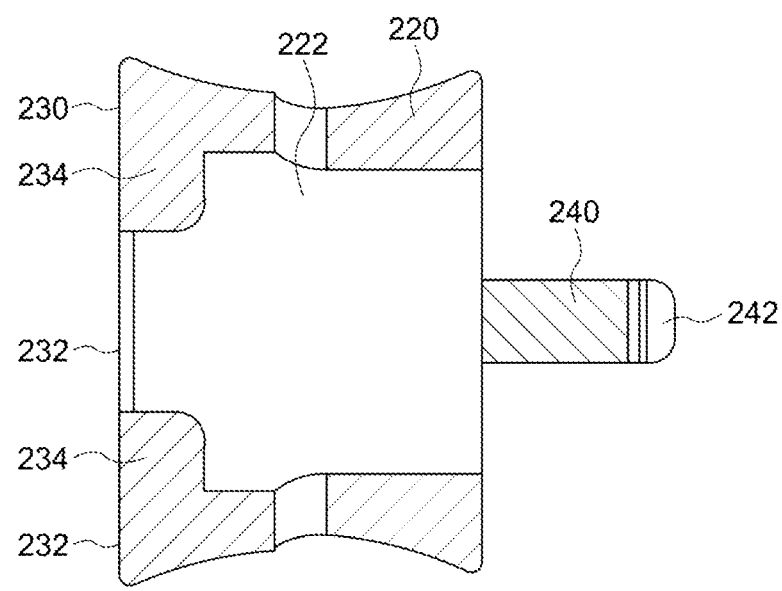
FIG. 2B depicts a cross-sectional view of the ratchet shifter shown in FIG. 2A rotated clockwise ninety degrees and taken along the plane 2-2.

FIGS. 2A and 2B illustrate one example of a ratchet shifter 200 constructed in accordance with one or more aspects of the present invention. As shown in FIG. 2A, ratchet shifter 200 includes a longitudinal axis 210, a proximal end 212 and a distal end 214. During assembly, longitudinal axis 210 aligns with longitudinal axis 1100 of handle 1000. Ratchet shifter 200 further comprises a body 220 defining a through-hole 222.

At proximal end 212, ratchet shifter 200 may include a ring-shaped outer surface 230 (as illustrated in FIG. 1A) having an opening 232 in communication with through-hole 222. As illustrated in FIGS. 1A and 2B, two guide projections 234 extend radially inward from outer surface 230 towards longitudinal axis 210. In one embodiment, guide projections 234 may appear as semi-circular in shape. In this example, guide projections 234 correspond to guide slots 370 (shown in FIG. 1A) on outer surface 326 of body 320 of tool connector 300 to provide a mating interface to allow for slidable engagement of guide projections 234 in guide slots 370, as discussed in more detail below. In alternative embodiments, the corresponding mating surfaces of guide projections 234 and guide slots 370 may have a different configuration or design than a semi-circular so long as guide projections 234 may slidably engage with guide slots 370 during assembly and operation.

As illustrated in FIG. 2A, ratchet shifter 200 may include two resilient and flexible clips 240 projecting longitudinally from distal end 214. Each clip 240 includes a proximal end 242 and a distal end 244. Proximal End 242 may be affixed to distal end 214. A lip 246 may extend radially inward from distal end 244 of each clip 240. Proximal portion 242 may include a flare at the bottom to form an annular fillet 250. Annular fillet 250 provides structural strength to clip 240 to resist shear and other forces that can otherwise cause clip 240 to break off from distal end 214 or otherwise fail.

Figure 3A:
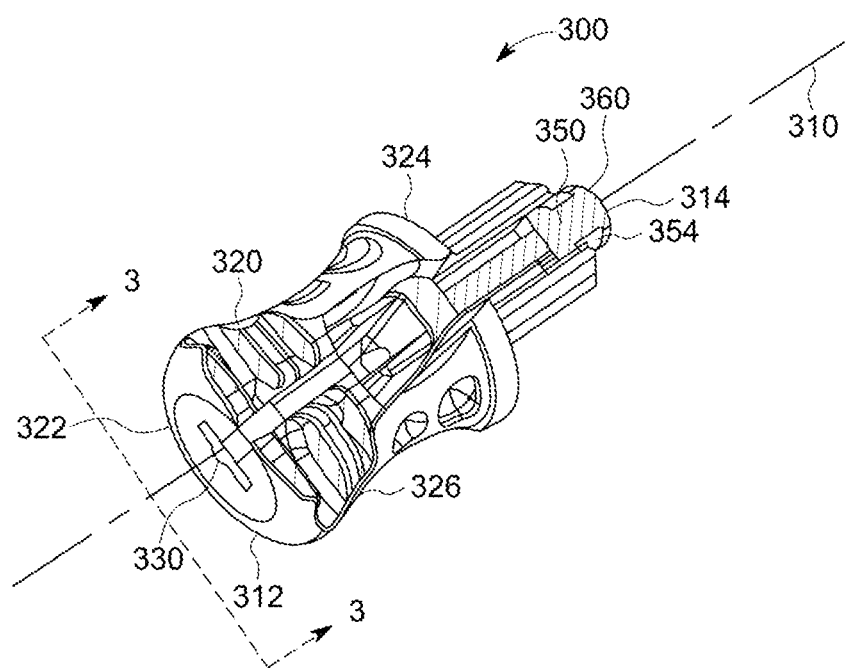
FIG. 3A depicts a perspective view of a tool connector for a handle constructed in accordance with one or more aspects of the present invention.
Figure 3B:
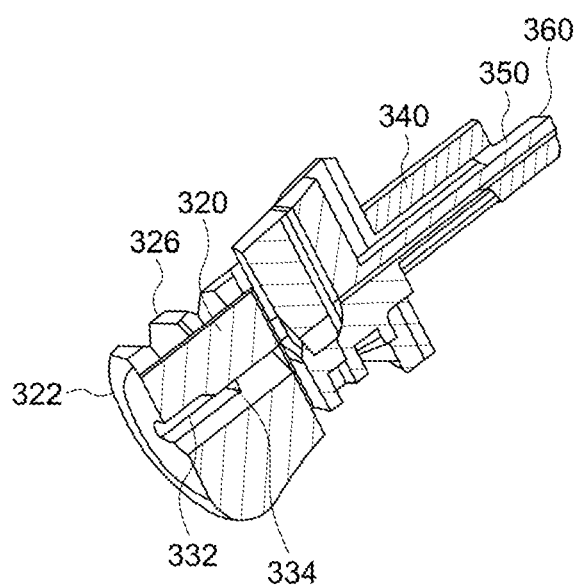
FIG. 3B depicts a cross-sectional view of the tool connector shown in FIG. 3A rotated counter-clockwise ninety degrees and taken along the plane 3-3.

FIGS. 3A and 3B illustrate one example of a tool connector 300 constructed in accordance with one or more aspects of the present invention. As shown in FIG. 3A, tool connector 300 includes a longitudinal axis 310, a proximal end 312 and a distal end 314. During assembly and operation, longitudinal axis 310 aligns with longitudinal axis 1100 of handle 1000. Tool connector 300 also includes a tool or instrument engagement body 320 extending from proximal end 312 and a mounting post 340 extending longitudinally from tool or instrument engagement body 320 to distal end 314.

Tool or instrument engagement body 320 includes a first side 322 at proximal end 312 and a second side 324 from which mounting post 340 extends therefrom. Tool or instrument engagement body 320 may include a longitudinal bore 332 in communication with tool engagement opening 330 disposed through at least a portion of body 320 along longitudinal axis 310 and shaped to receive and removably couple or retain a drive shank of a surgical tool or instrument, such as, for example, a drill or a screwdriver.

There are many coupling mechanism known in the art that removably couple or retain a surgical tool or instrument during use. As one example, a drive shank or end of a surgical tool or instrument (not shown), such as, for example, a drill bit or screwdriver, is removably grasped or coupled within longitudinal bore 332 formed in tool or instrument engagement body 320. The drive shank of the surgical tool or instrument may be inserted into longitudinal bore 332 until the end of the drive shank or an aspect of the drive shank contacts a stop 334, at which point further insertion may be prevented. In one example, as drive shank is being fully inserted into longitudinal bore 332, a living hinge resiliently attached to body 320 is adapted to cooperate with a corresponding groove or indentation on the outer surface of the drive shank inserted into longitudinal bore 332 of the tool or instrument engagement body 320. In this example, the living hinge may be accessible through a transverse opening formed in the side surface of tool or instrument engagement body for manual engagement by a user. In alternative embodiments, tool or instrument engagement body 320 may include a chuck to removably grasp the drive shank of the surgical tool or instrument. In other embodiments, tool or instrument engagement body may removably couple to the tool or instrument drive shank by an AO, square drive or Hudson style orthopedic instrument connection known in the art.

As illustrated in FIG. 1A, tool engagement body 320 may include two guide slots 370 formed in outer surface 326 of body 320 and extending radially inward. As discussed above, the profile of guide slots 370 correspond to two guide projections 234 of ratchet shifter 200 to allow slidable engagement of guide projections 234 in guide slots 370 during assembly and operation.

Figure 3C:
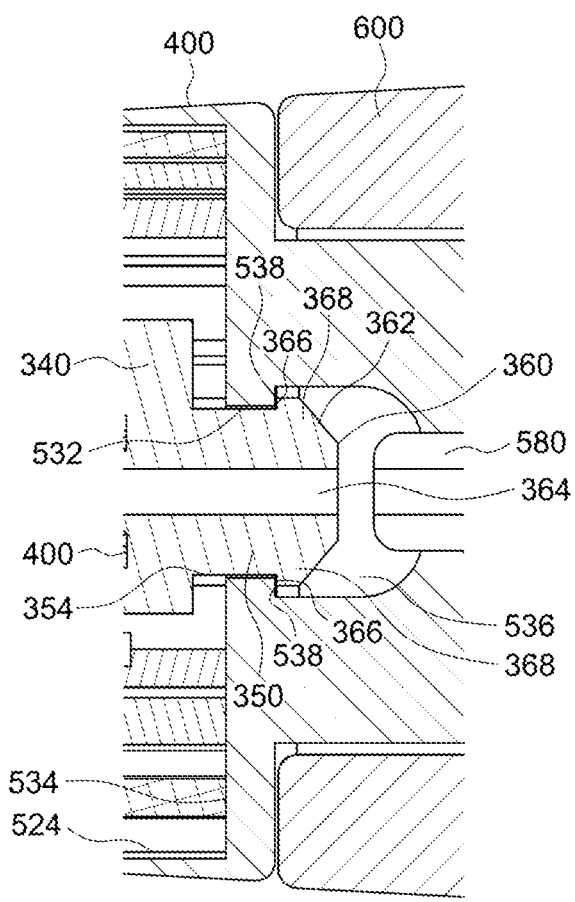
FIG. 3C depicts a partial cross-sectional view taken from the bracketed section in FIG. 8B illustrating one example of a coupling mechanism attaching a distal end of a tool connector to a rear power housing constructed in accordance with one or more aspects of the present invention.

Mounting post 340 comprises, at distal end 314, a pedestal 350 and a cap 360. Pedestal 350 and cap 360 are configured for acceptance into a through-hole 532 formed in retainer base 530 of rear power housing 500, as illustrated in FIG. 3C. Pedestal 350 is attached to and extends longitudinally from mounting post 340. Pedestal 350 can have a variety of transverse heights depending upon the particular application and the particular dimensions of retainer base 530. The illustrated pedestal 350 has a generally cylindrical shape, but can be configured in a variety of other shape, which can match the shape of through-hole 532 formed in retainer base 530 of rear power housing 500.

Cap 360 extends radially outward from the top portion of pedestal 350. Cap 360 assists in coupling mounting post 340 of tool connector 300 to retainer base 530 of rear power housing 500 by preventing separation of pedestal 350 from retainer base 530. The illustrated cap 360 has a cross-sectional shape generally similar to that of pedestal 350 for ease of manufacture, however, it can be configured in a variety of other cross sectional shapes to generally match the shape of through-hole 532 in retainer base 530, which is described below. Cap 360 desirably extends beyond the circumference of pedestal 350 by a lip 368 to assist in securely coupling mounting post 340 to retainer base 530, and to prevent translational movement relative to each other. In other embodiments, cap 360 need not circumscribe the entire pedestal 350 and can, for example, comprise only one or more radial members that extend radially outwardly from pedestal 350. The transverse thickness of cap 360 is sufficient to perform its structural function of coupling mounting post 340 to retainer base 530 without significantly bending or breaking.

A chamfer 362 may be formed on an upper peripheral edge of cap 360 to assist in the assembly of mounting post 340, as described below. In one example, the illustrated chamfer 362 transversely extends about one-half the thickness of cap 360. In an embodiment, pedestal 350 and cap 360 further include a hole or slot 364 extending axially through at least a portion of cap 360 and pedestal 350. Hole or slot 364 facilitates coupling between mounting post 340 and retainer base 530 via through-hole 532 in retainer base 530 by allowing cap 360 and at least a portion of pedestal 350 to flex radially inwards as cap 360 is urged through the through-hole 532 during assembly, as described below.

Pedestal 350 desirably has a smooth side surface 354 to facilitate sliding and rotation of pedestal 350 relative to retainer base 530, such that pedestal 350 provides a bearing surface for retainer base 530. Lip 368 of cap 360 may include a flat underside surface 366 to match the configuration of a contacting surface 538 of retainer base 530 past through-hole 532 to provide a flush surface and bearing surface for rotation of tool connector 300 relative to rear power housing 500, as described below. In the illustrated example, pedestal 350 and cap 360 have a one-piece configuration for ease of manufacture and strength; however, pedestal 350 and cap 360 can alternatively comprise a two-piece configuration extending from or attached to mounting post 340. Although pedestal 350 and cap 360 is generally mushroom shaped, pedestal 350 and cap 360 can also be generally T-shaped, inversely L-shaped and the like.

Pedestal 350 and cap 360 are desirably formed in unity with mounting post 340 for structural strength. However, pedestal 350 and cap 360 can comprise separate components. The illustrated pedestal 350, cap 360 and through-hole 532 of retainer base 630 have a circular configuration, with the longitudinal axis of both pedestal 350, cap 360 and through-hole 532 of retainer base 530 being aligned with longitudinal axis 1100 of handle 1000 so that tool connector 300 can centrally rotate.

In the illustrated embodiment, as best shown in FIG. 3C, retainer base 530 of rear power housing 500 has a through-hole 532 sized and configured to receive pedestal 350 and more preferably to generally match that of pedestal 350 so that tool connector 300 can rotate relative to rear power housing 600 about pedestal 350. The illustrated through-hole 532 extends through retainer base 530 and has a first diameter. Through-hole 532 communicates with retainer space 536 that may have a second diameter. In one embodiment, first diameter is slightly larger than that of pedestal 350 and second diameter of retainer space 536 may be slightly larger than that of cap 360 with lip 368. Like pedestal 350, through-hole 532 has a smooth surface to minimize friction when tool connector 300 is rotated. In one embodiment, a chamfer (not shown) may circumscribe the lower portion of first diameter or entrance from cavity 540 of through-hole 532 to assist in the assembly of the rotatable mounting post 340 of tool connector 300, as described below.

When assembled, pedestal 350 and cap 360 are inserted and transversely advanced along axis 510 into through-hole 532 and secured to retainer base 530. In particular, cap 360 is housed within retainer space 536 of retainer base 530 with the underside surface 366 of lip 368 of cap 360 being generally flush with contacting surface 538 in retainer space 536. Chamfer 362 that circumscribes cap 360 allows cap 360 to deform or radially displace inward and advance through through-hole 532, aided, in some embodiments with, for example, a chamfer (not shown) that circumscribes the entrance of through-hole 532 from cavity 540. Once cap 360 passes through through-hole 532, cap 360 bounces back to its original configuration and underside surface 366 of lip 368 meshes with contacting surface 538 in retainer space 536, while pedestal 350 extends through through-hole 532. By this configuration, tool connector 300 can rotate three hundred and sixty degrees relative to rear power housing 500.

Figure 4A:
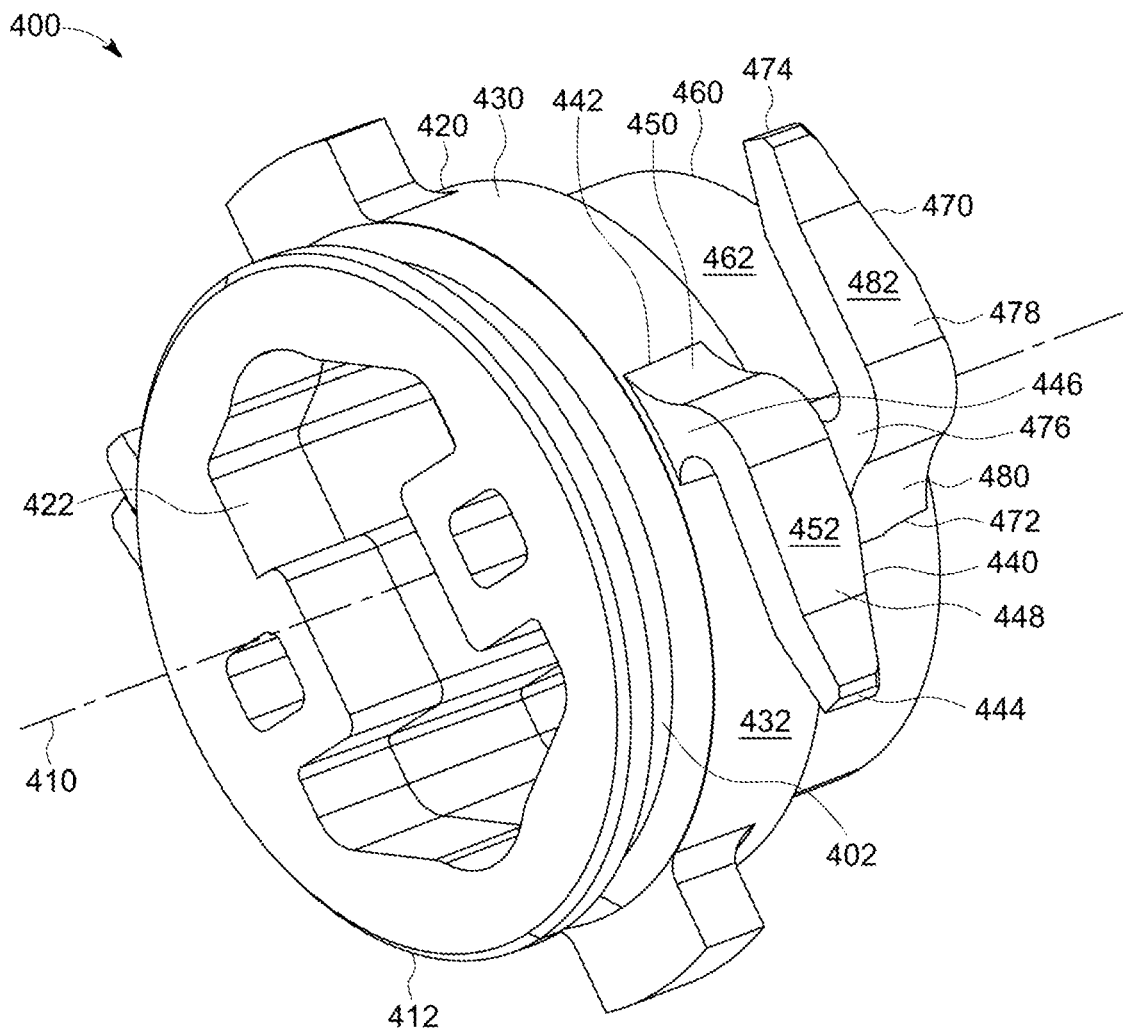
FIG. 4A depicts a perspective view of a ratchet coupler for a handle constructed in accordance with one or more aspects of the present invention.
Figure 4B:
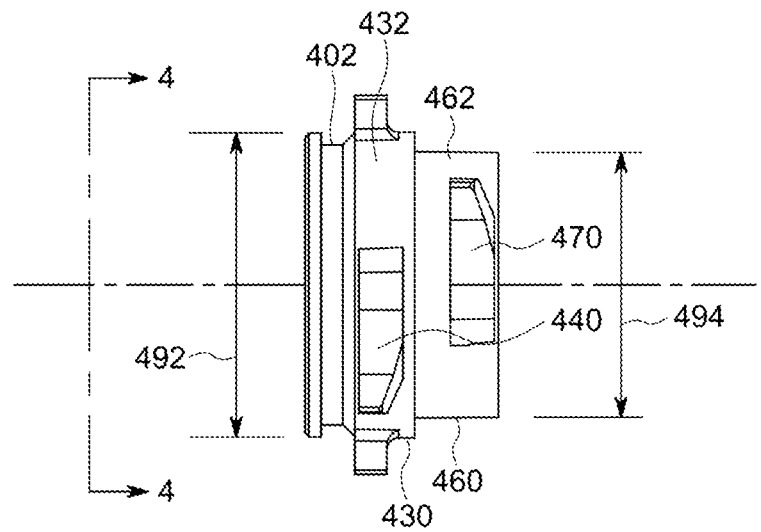
FIG. 4B depicts a side view of the ratchet coupler shown in FIG. 4A.
Figure 4C:
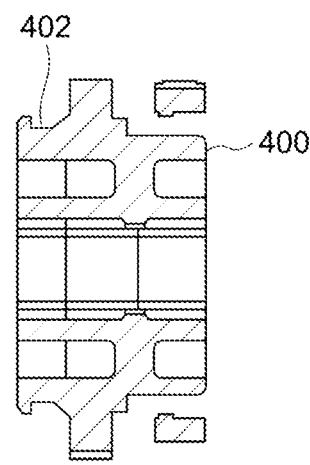
FIG. 4C depicts a cross-sectional view of the ratchet coupler shown in FIG. 4B rotated clockwise ninety degrees and taken along the plane 4-4.

FIGS. 4A-4C illustrate one example of a ratchet coupler 400 constructed in accordance with one or more aspects of the present invention. Ratchet coupler 400 includes a longitudinal axis 410, a proximal end 412 and a distal end 414. During operation, longitudinal axis 410 aligns with longitudinal axis 1100 of handle 1000. Ratchet coupler 400 also comprises a body 420 defining a longitudinal through-hole 422. Longitudinal through-hole 422 is configured and shaped to slidably receive mounting post 340 of tool connector 300 during assembly. Through-hole 422 is also configured and shaped so that ratchet coupler 400 will simultaneously rotate with tool connector 300 during operation of handle 1000. Ratchet coupler 400 may also include a circumferential groove 402 formed in its outer surface near proximal end 412.

As illustrated in FIGS. 4A and 4B, body 420 may include a first forward portion 430 and a second rear portion 460. First forward portion 430 includes an outer surface 432 and a first diameter 492. Second rear portion 460 includes an outer surface 462 and a second diameter 494. First diameter 492 may be different than second diameter 494. In one example, as illustrated in FIG. 4B, first diameter 492 is greater than second diameter 494. An embodiment having first forward portion 430 and second rear portion 460 with different diameters may assist in ensuring that ratchet coupler 400 is properly fitted within rear power housing 500 during assembly.

In one embodiment, illustrated in FIGS. 4A and 4B, first forward portion 430 may include a plurality of hinges or fingers 440 project radially outward from outer surface 432. In one example, as shown in FIG. 4A, there may be two fingers or hinges 440 spaced radially equidistant from around outer surface 432. Each hinge or finger 440 includes a proximal end 442, a distal end 444, a proximal portion 446 directly affixed to outer surface 432 at proximal end 442 and extending radially outward from outer surface 432, and a distal portion 448 extending from proximal portion 446 towards distal end 444. Proximal portion 446 may include a flare at the bottom to form an annular fillet 450. Annular fillet 450 provides structural strength to finger or hinge to resist shear and other forces that can otherwise cause finger or hinge 440 to break off from outer surface 432 of first forward portion 430 or otherwise fail. Distal portion 448 may include a radially outward facing surface 452. Distal portion 448 may bend at an angle relative to proximal portion 446 and further extend circumferentially around or followed around the circumference of a first forward portion 430. In one example, distal portion 448 of each hinge or finger 440 extend circumferentially around in a clockwise direction relative to longitudinal axis 410, as shown in FIG. 4A.

In one embodiment, illustrated in FIGS. 4A and 4B, second portion 460 may include a plurality of hinges or fingers 470 project radially outward from outer surface 462. In one example, as shown in FIG. 4A, there may be two fingers or hinges 470 spaced radially equidistant from around outer surface 462. Each hinge or finger 470 includes a proximal end 472, a distal end 474, a proximal portion 476 directly affixed to outer surface 462 at proximal end 472 and extending radially outward from outer surface 462 and a distal portion 478 extending from proximal portion 476 towards distal end 474. Proximal portion 476 may include a flare at the bottom to form an annular fillet 480. Annular fillet 480 provides structural strength to finger or hinge to resist shear and other forces that can otherwise cause finger or hinge 470 to break off from outer surface 462 of second rear portion 460 or otherwise fail. Distal portion 478 may include a radially outward facing surface 482. Distal portion 478 may bend at an angle relative to proximal portion 446 and further extend circumferentially around or followed around the circumference of a second rear portion 460. In one example, distal portion 478 of each hinge or finger 470 extend circumferentially around in a counter-clockwise direction relative to longitudinal axis 410, as shown in FIG. 4A.

As will be discussed in more detail below, plurality of fingers or hinges 440, 470 may be spaced radially equidistant from one another to allow the engagement between each finger or hinge 440, 470 and teeth 560, 561, respectively, on forward circumferential surface 542 and rear circumferential surface 546, respectively, of cavity 540 of rear power housing 500. Each finger or hinge 440, 470 is resilient, flexible and biased radially outward from longitudinal axis 410 of ratchet coupler 400. In one example, fingers or hinges 440, 470 are integral with first forward portion 430 and second rear portion 460, respectively, and formed during the same injection molding process. In alternative embodiments, fingers or hinges 440, 470 may be created by additive manufacturing or may be metallic members that are assembled or molded by, for example, insert molding, to outer surfaces 432, 462 of ratchet coupler 400.

While the illustrated embodiment may have two fingers or hinges 440 equidistantly spaced from one another around outer surface 432 and two fingers or hinges 470 equidistantly spaced from one another around outer surface 462, a plurality of offset distances may be used as well to achieve substantially the same result or a different desired result. Further, the number of fingers/hinges 440, 470 and/or the thickness and width of each finger or hinge 440, 470 may be "tuned" or vary greatly depending on the particular load or force desired for a particular application (e.g. desired torque for fingers or hinges 440, 470 to ratchet over the teeth of rear power housing 500 in a particular direction) by each finger or hinge 440, 470. The particular number, configuration and design of the plurality of fingers or hinges 440, 470 can be varied to accommodate the various loads or forces that may be needed or desired therethrough during operation of handle 1000.

Figure 5A:
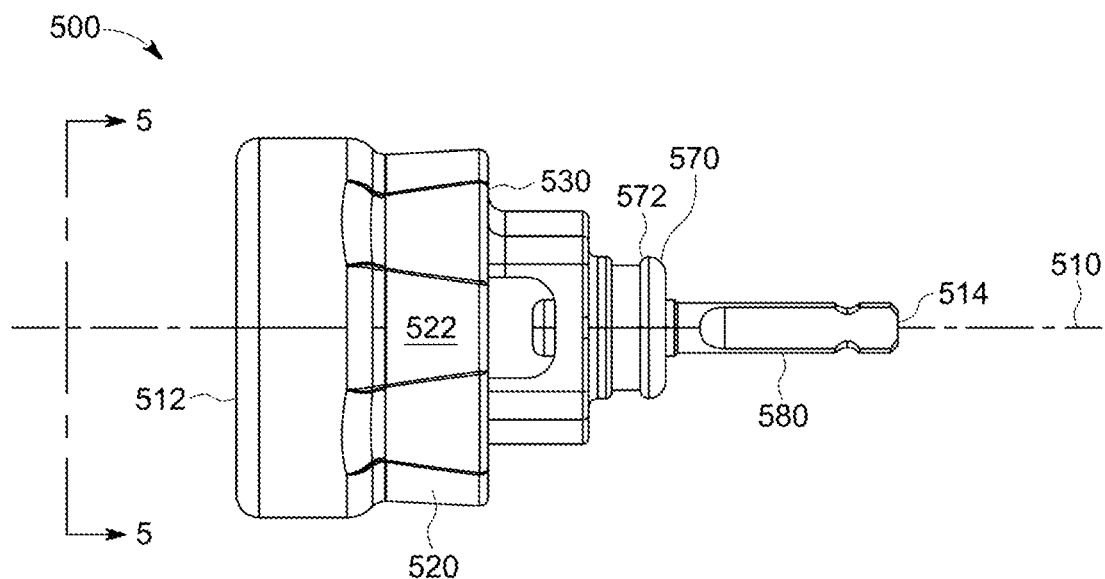
FIG. 5A depicts a side view of a rear power housing for a handle constructed in accordance with one or more aspects of the present invention.
Figure 5B:
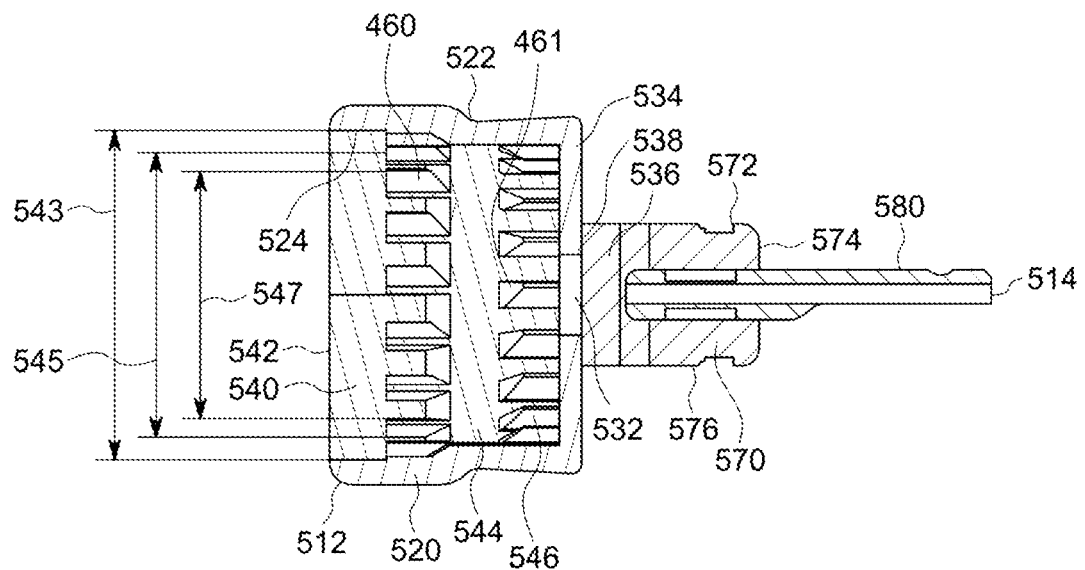
FIG. 5B depicts a cross-sectional view of the rear power housing shown in FIG. 5B taken along the plane 5-5.

FIGS. 5A and 5B illustrate one example of a rear power housing 500 constructed in accordance with one or more aspects of the present invention. Rear power housing 500 includes a longitudinal axis 510, a proximal end 512 and a distal end 514. During operation, longitudinal axis 510 aligns with longitudinal axis 1100 of handle 1000 during assembly and use. As illustrated in FIG. 5A, rear power housing 500 comprises body 520 extending from proximal end 512 a drive shank base 570 extending from body 520, and a drive shank 580 extending from drive shank base 570 longitudinally towards distal end 514.

As illustrated in FIG. 5A, body 520 is generally cylindrical in shape that may include a side wall 522 and a retainer base 530 that together define a longitudinal cavity 540 open at proximal end 512. Cavity is configured and shaped to receive ratchet coupler 400, as will be discussed in detail below. Cavity 540 communicates with a retainer space 536 via through-hole 532. Cavity 540 is defined by interior surface 524 of side walls 522 and inner surface 534 of retainer base 530. Retainer space 536 is defined by contacting surface 538 and drive shank base 570. Drive shank base 570 permanently couples or holds drive shank 580.

As shown in FIG. 5B, interior surface 524 of side wall 522 includes a forward circumferential surface 542 having a first diameter 543, a neutral circumferential surface 544 having a second diameter 545 and a rear circumferential surface 546 having a third diameter 547. In one embodiment, as illustrated in FIG. 5B, first diameter 543 is greater than second diameter 545 and third diameter 547, and second diameter 545 is greater than third diameter 547.

Figure 8A:
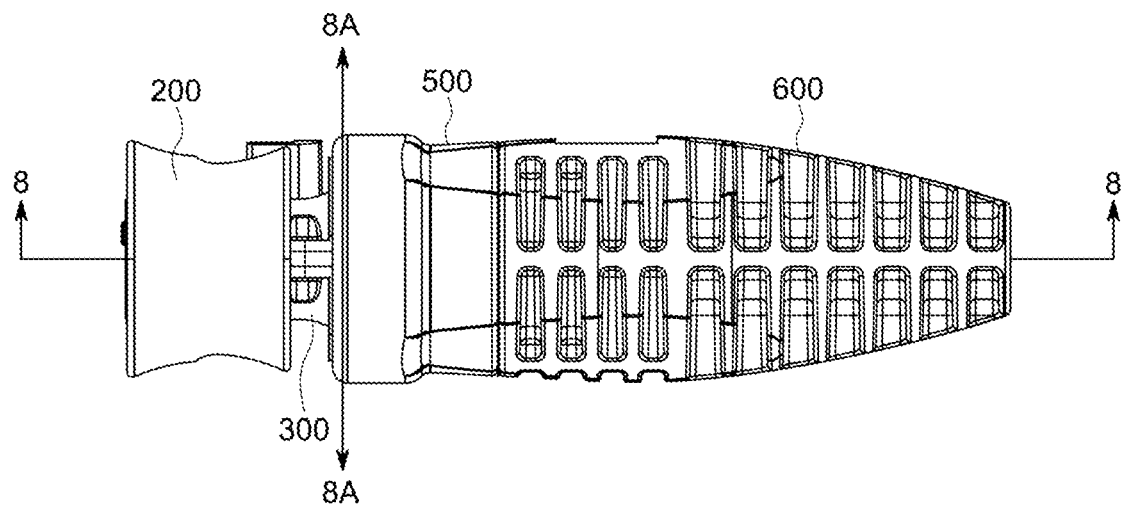
FIG. 8A depicts a side view of one embodiment of an assembled handle in a forward position with one example of an optional handle grip constructed in accordance with one or more aspects of the present invention.
Figure 8B:
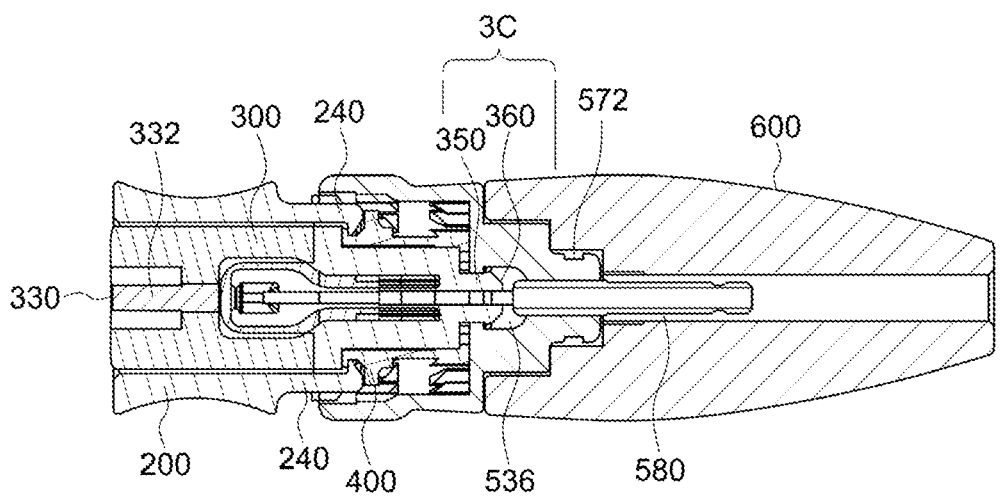
FIG. 8B depicts a cross-sectional view of the assembled handle shown in FIG. 8A taken along the plane 8-8.
Figure 8C:
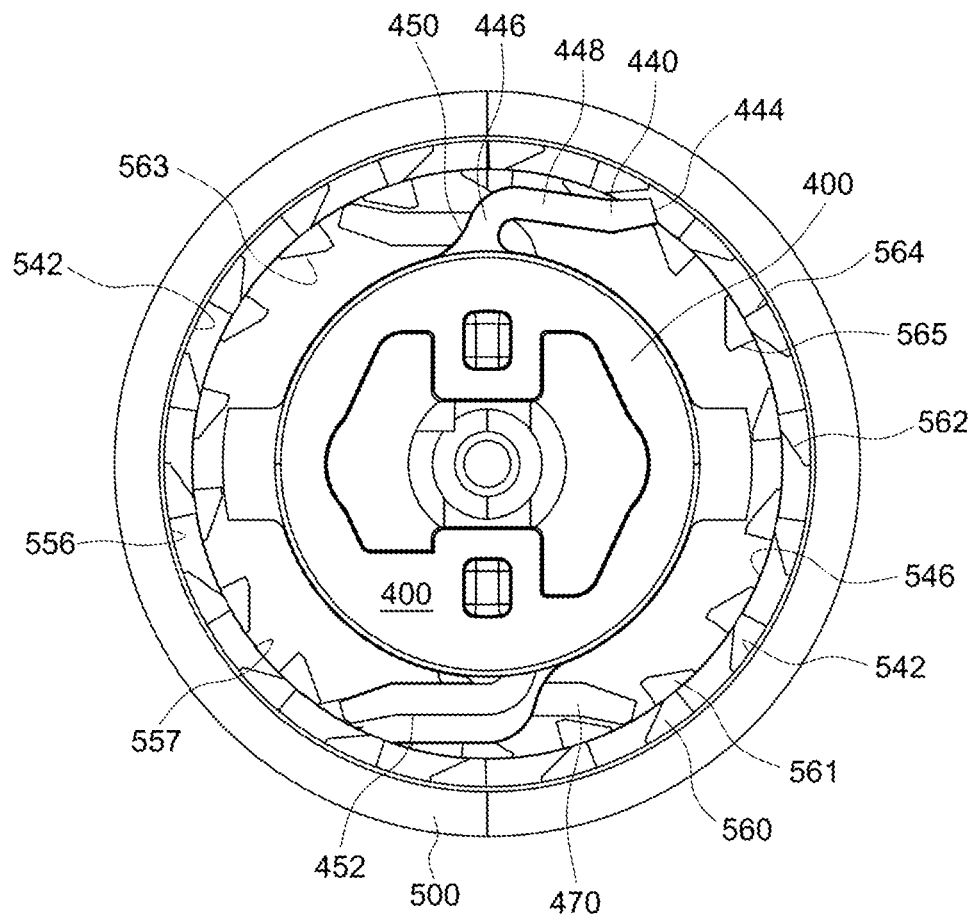
FIG. 8C is a cross-sectional view of the assembled handle shown in FIG. 8A taken along the plane 8A-8A.
Figure 9A:
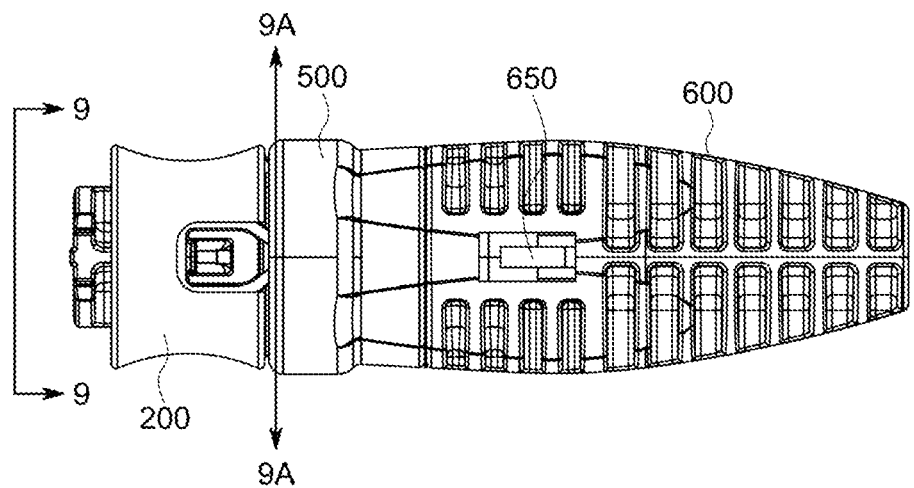
FIG. 9A depicts a side view of an assembled handle in the reverse position for use with a power tool constructed in accordance with one or more aspects of the present invention.
Figure 9B:
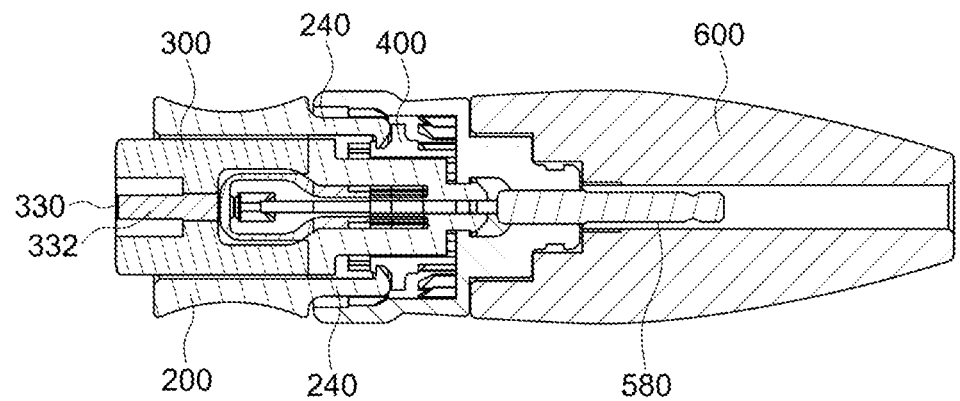
FIG. 9B depicts a cross-sectional view of the assembled handle shown in FIG. 9A taken along the plane 9-9.
Figure 9C:
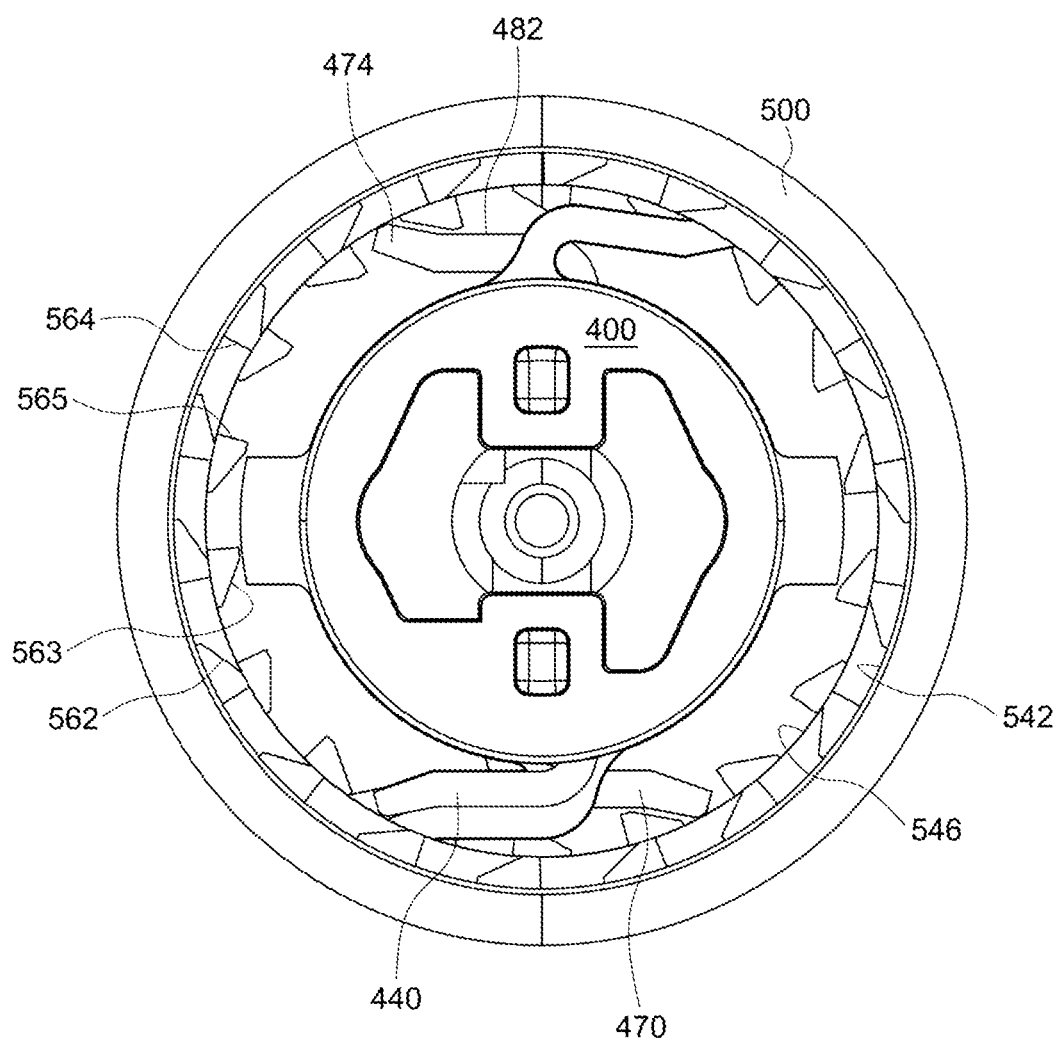
FIG. 9C depicts a cross-sectional view of the assembled handle shown in FIG. 9A taken along the plane 9A-9A.

As illustrated in FIGS. 5B, 8C and 9C, forward circumferential surface 542 includes a plurality of teeth 560 projecting radially inward towards longitudinal axis 510. Plurality of teeth 560 are spaced radially equidistant or disposed at intervals in the circumferential direction around and extend axially along forward circumferential surface 542. As illustrated clearly in FIG. 8C, each tooth 560 includes an inclined surface 562 and a stop surface 564. Inclined surfaces 562 angle radially inward in a counter-clockwise direction to create a ramp. Stop surfaces 564 extend radially outward from forward circumferential surface 542 and substantially transverse to longitudinal axis 510. A slots or spaces 566 may be formed by forward circumferential surface 542 between a stop surface 564 of one tooth 560 and an inclined surface 562 of an adjacent tooth 560.

As illustrated in FIGS. 5B, 8C and 9C, rear circumferential surface 546 includes a plurality of teeth 561 projecting radially inward towards longitudinal axis 510. Plurality of teeth 561 are spaced radially equidistant or disposed at intervals in the circumferential direction around and extend axially along rear circumferential surface 546. As illustrated clearly in FIG. 8C, each tooth 561 includes an inclined surface 563 and a stop surface 565. Inclined surfaces 563 angle radially inward in a clockwise direction to create a ramp. Stop surfaces 565 extend radially outward from rear circumferential surface 546 and substantially transverse to longitudinal axis 510. A slot or space 567 may be formed by rear circumferential surface 546 between a stop surface 565 of one tooth 561 and an inclined surface 563 of an adjacent tooth 561.

In one embodiment, teeth 560 and 561 are molded such that the nominal diameter of teeth 560 is different from the nominal diameter of teeth 561. The particular number, configuration and design of the plurality of teeth 560, 561 may be varied to accommodate the various loads or forces that may be needed or desired therethrough during operation of handle 1000. Further, the number of teeth 560, 561 and/or the height and length of inclined surfaces 562, 563 of each tooth 560, 561, respectively, may be "tuned" or vary greatly depending on the particular ratchet load or force desired for a particular application (e.g. desired ratchet force for fingers or hinges 440, 470 to overcome or pass over teeth 560, 561 of rear power housing 500 in a particular direction).

Drive shank 580 may be configured and designed to couple to various types of power instruments to drive handle 1000. For example, as illustrated in FIG. 5A, drive shank 580 comprises be a hex drive shank that includes a quick connect feature. A hex drive shank design provides for high torque transmission and have no need to be tightened. A hex drive shank design also does not allow for slipping commonly experienced with straight cylindrical drive shanks. In alternative embodiments, drive shank may be in the form of other known drive shank shapes, such as, for example, SDS drive shanks, straight drive shanks, square drive shank, triangle drive shanks or the like. Drive shank may also be designed to be, for example, removably coupled to power instruments comprising one of an AO, square drive, or Hudson® style orthopedic instrument connection.

In one embodiment, rotation can be applied to rear power housing 500 either directly to drive shaft 580 by, for example, a power instrument, or directly to other aspects of rear power housing 500 (e.g. drive shank base) by, for example, manual rotation to handle grip 600.

Figure 6A:
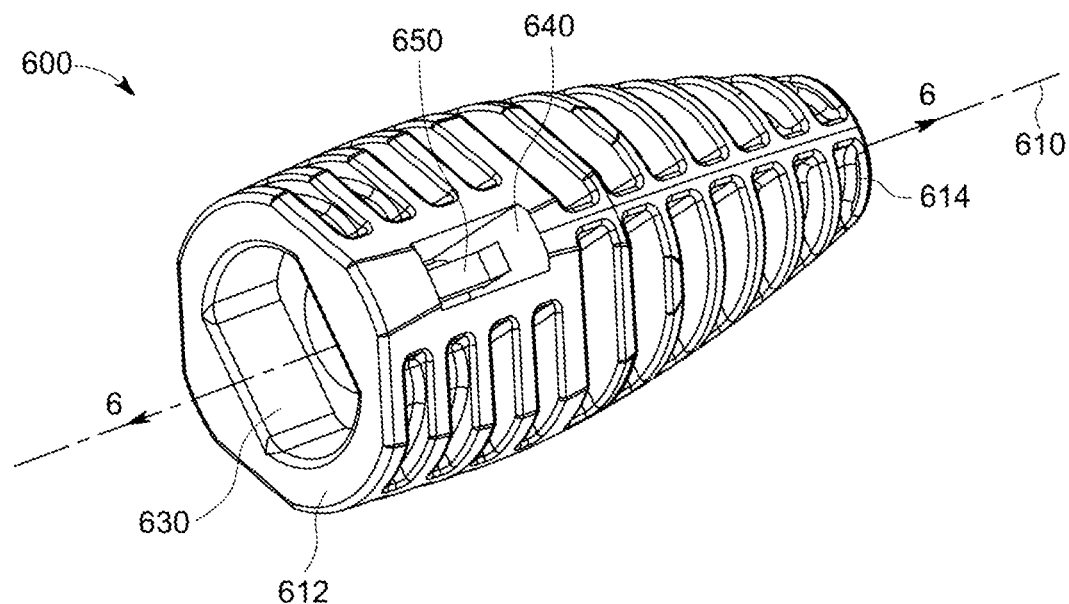
FIG. 6A depicts a perspective view of one example of an optional handle grip for a handle constructed in accordance with one or more aspects of the present invention.
Figure 6B:
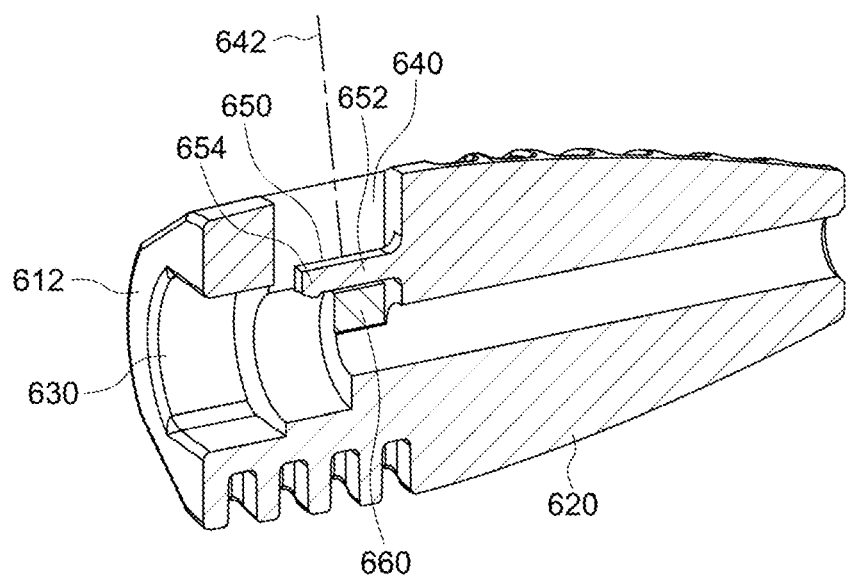
FIG. 6B depicts a cross-sectional view of the handle grip shown in FIG. 6B rotated counter-clockwise ninety degrees and taken along the plane 6-6.
Figure 6C:
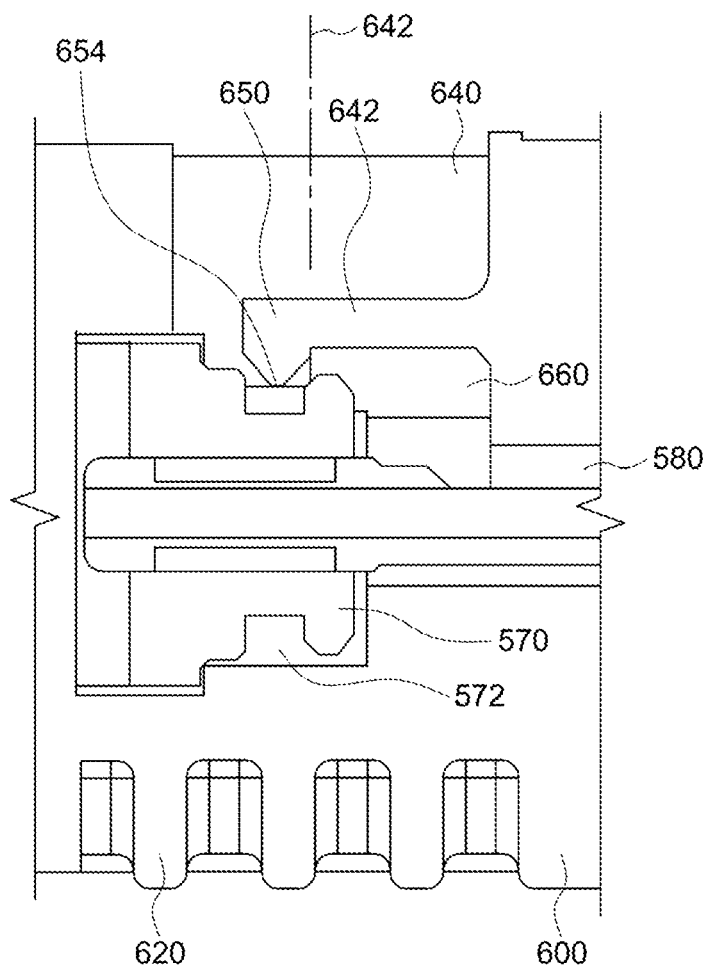
FIG. 6C depicts a partial cross-sectional view of the handle grip shown in FIG. 6A illustrating one example of a coupling mechanism to removably couple a drive shaft base of a rear power housing constructed in accordance with one or more aspects of the present invention.
Figure 7A:
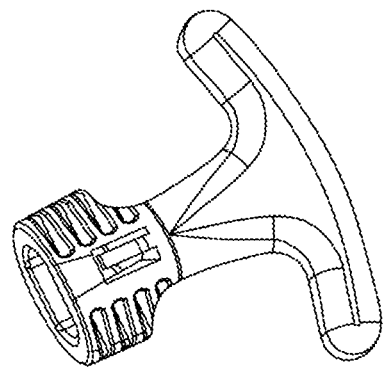
FIG. 7A depicts a perspective view of an alternative embodiment of a handle grip for a handle constructed in accordance with one or more aspects of the present invention.
Figure 7B:
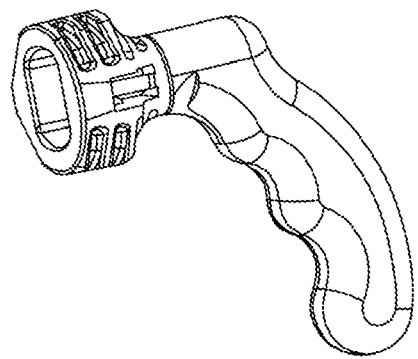
FIG. 7B depicts a perspective view of an alternative embodiment of a handle grip for a handle constructed in accordance with one or more aspects of the present invention.
Figure 7C:
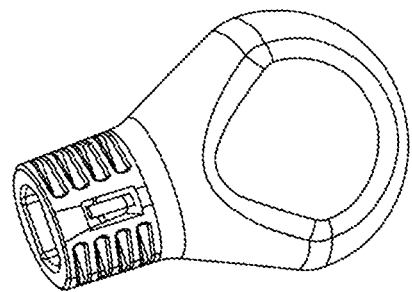
FIG. 7C depicts a perspective view of an alternative embodiment of a handle grip for a handle constructed in accordance with one or more aspects of the present invention.

FIGS. 6A and 6B illustrate a perspective and cross-sectional view, respectively, of one example of an optional handle grip 600 constructed in accordance with one or more aspects of the present invention. As illustrated in FIG. 6A, handle grip 600 may include a body 620 having a longitudinal axis 610, a proximal end 612 and a distal end 614. During assembly and operation, longitudinal axis 610 aligns with longitudinal axis 1100 of handle 1000. One example, as illustrated in FIG. 6A, body 620 may have a bulbous shape suitable for being held by a human hand. Other examples of body-shapes for handle grip 600 are illustrated in FIGS. 7A-6C, which include, for example, a T-handle configuration (FIG. 7A), a pistol grip (FIG. 7B) or a palm handle (FIG. 7C). Handle grip 600 may also be in the form of, for example, a ball or any other various shaped configurations that permit a user to manually manipulation allowing torque to be applied to the surgical instrument or tool attached to handle. In other embodiments, handle grip 600 may be customizable in applications for various commercial marketing purposes with respect to, for example, color, marking and texture.

Body 620 of handle grip 600 may have a light weight, inexpensive, biologically inert material. In one example, handle grip 600 may be made from polyacrylamide, polycarbonate or acrylonitrile butadiene styrene ("ABS"). Handle grip 600 may also be a uni-body or monolithic design as shown in FIG. 6A. This uni-body construction makes handle grip 600 easier to manufacture and stronger than a multicomponent design having the same materials of construction.

Handle grip 600 may include a longitudinal bore 630 disposed through handle grip 600 along longitudinal axis 610. Longitudinal bore 630 is open at proximal end 612 of handle grip 600.

Handle grip 600 may also include a transverse bore 640. Transverse bore 640 is disposed through body 620 of handle grip 600. Transverse bore 640 may have a longitudinal axis 642. Transverse bore 640 intersects with longitudinal bore 630. In one example, transverse bore 640 is perpendicular to longitudinal bore 630. Transverse bore 640 may also have a first opening that opens out of body 620 and a second opening communicating with longitudinal bore 630.

Handle grip 600 further may include a button 650. In one embodiment, button 650 is flexibly attached to handle grip 600, as shown in FIG. 6B. Button 650 may extend through transverse bore 640, intersecting longitudinal bore 630. Button 650 and transverse bore 640 may be disposed on body 620 of handle grip 600 such that button 650 is thumb accessible and/or depressible. Positioning button 650 closer to proximal end 612 of handle grip 600, also positions button 650 closer to the portion of handle grip 600 that engages with groove 572 formed in drive shank body 570 of rear power housing 500. Handle grip 600 may be configured (e.g. shaped and dimensions) to allow handle grip 600 to be held, grasped, or used by a hand such that the fifth digit and hypothenar region are positioned in proximity to or around the distal end 614 of handle grip 600, with handle grip 600 extending across the palm and in the direction of the region between the first and second digit, such that the first digit or thumb may easily access and depress button 600.

Advantageously, because of the uni-body design, devices made in accordance with the present invention may not have additional components such as springs. Button 650 is connected to body by resilient member 652. Thus, a handle grip 600 constructed in accordance with one or more aspects of the present invention may be less expensive to manufacture and simple to use. Moreover, because the handle grip 600 is inexpensive to make, it is an ideally suited single use (e.g. disposable) device. Cleanliness is assured because the handle grip 600 is removed from a sterile package and used only once.

Referring now to FIG. 6B, there is shown a cross-sectional view of a handle grip 600 constructed in accordance with one or more aspects of the present invention. As illustrated, handle grip 600 includes a backstop 660 disposed within longitudinal bore 630. Button 650 may also have a thickness which may extend into transverse bore 640 in a longitudinal direction relative to longitudinal axis 642. In one embodiment, button 650 includes a distal end having a lip 654. Lip 654 projects and is normally biased radially downward towards longitudinal axis 612 of handle grip 600. In one embodiment, button 650 with lip 654 creates a living hinge when coupled to rear power housing 500.

Referring to FIG. 6C, drive shank 580 of rear power housing 500 can be inserted through proximal end 612 into longitudinal bore 630 of handle grip 600. Drive shank 580 of rear power housing 500 may be inserted into longitudinal bore 630 until end surface 574 of drive shank base 570 of rear power housing 500 contacts boss 660 or, alternatively, until contacting surface 538 of retainer base 530 of rear power housing 500 contacts proximal end 612 of handle grip 600, at which point further insertion may be inhibited. As drive shank 580 is being fully inserted into longitudinal bore 630, lip 654 of button 650 slides into groove 572 formed on the outer surface 576 of drive shank base 570 of rear power housing 500. Lip 654 of button 650 is adapted to cooperate with corresponding groove or indentation 572 on outer surface 576 of drive shank base 570 of rear power housing 500 inserted into longitudinal bore 630 of handle grip 600.

Once drive shank 580 and drive shank base 570 of rear power housing 500 is inserted into handle grip 600, lip 654 of button 650 is biased or displaced radially into groove 572. In one embodiment, a "clicking" sound may be heard when lip 654 fully engages groove 572. However, a user may disengage rear power housing 500 from handle grip 600 by forcibly pulling out rear power housing 500 from handle grip 600 such that lip 654 pivots out of groove 572 of drive shank base 570 of rear power housing 500. Rear power housing 500 may connect with lip 654 fitted into groove 572 providing significant resistance to disengagement forces. However, rear power housing 500 may still be pulled in response to significant force being applied by a user to rear power housing 500 through handle grip 600. In one example, a transverse force may be applied to drive shank base 570 of rear power housing 500 by depressing button 650, providing additional force to prevent rear power housing 500 from being pulled out by disengagement forces.

In other embodiments, handle grip 600 may include more than one buttons or living hinges 630 engaged with groove 572 formed in drive shank base 570 of rear power housing 500. Alternatively, other coupling mechanisms may be applied to drive shank 580 or drive shank base 570 of rear power housing 500 to removably retain within handle grip 600 during use. For example, the coupling mechanisms described and illustrated in WO2019/168987, which is hereby incorporated herein by reference, may be used. In alternative embodiments, the coupling mechanism may include a chuck to removably grasp the drive shank of the surgical tool or instrument. In other embodiments, drive shank 580 may removably couple within handle grip 600 by an AO, square drive or Hudson style orthopedic instrument connection known in the art.

When assembled, ratchet coupler 400 is slide over mounting post 340 of tool connector 300. In one embodiment, first forward portion 430 with its larger first diameter 492, as compared to second diameter 494 of second forward portion 460, is inserted first over distal end 312 of tool connector 300 to prevent ratchet coupler 400 from being assembled backwards.

Next, distal end 214 of ratchet shifter 200 is configured to slide over proximal end 312 of tool connector 300. As ratchet shifter 200 is being slid over tool connector 300, guide projections 234 align with and are slidably received by guide slots 370. Clips 240 of ratchet shifter 200 engage groove 402 of ratchet coupler 400. In one example, clips 240 flex radially outward as proximal end 412 of ratchet coupler 400 is configured to slide longitudinally on mounting post 340 of tool connector 300 to couple with ratchet shifter 200. A chamfer 241 may be formed at distal end 244 of clip 240 to assist in distal end 244 of clip 240 get past proximal end 412 of ratchet coupler 400 until lip 242 of clip 240 snaps back or flexes or displaces radially inward into groove 402 of ratchet coupler 400. In one example, lip 242 and groove 402 form a living hinge to couple together ratchet shifter 200 and ratchet coupler 400. When ratchet shifter 200 and ratchet coupler are coupled together in this manner, ratchet coupler 400 (with ratchet shifter attached) is still able to slide, but not rotate, on mounting post 340 of tool connector 300.

After the assembly of ratchet shifter 200, tool connector 300 and ratchet coupler 400, distal end 314 of tool connector 300 is then inserted axially along longitudinal axis 510 into cavity 540 formed in body 520 of rear power housing 500. As distal end 314 is advanced into cavity 540, mounting post 340 with ratchet coupler 400 are also inserted into cavity 540 of tool connector 300. Pedestal 350 and cap 360 at distal end 314 of tool connector 300 are inserted and transversely advanced into through-hole 532 formed in retainer base 530 of rear power housing 500. Cap 360 is advanced completely through through-hole 532 until cap 360 radially displaces and is housed completely within retainer space 536 with underside surface 366 of lip 368 of cap 360 being generally flush with contacting surface 538 of retainer base 530 in retainer space 536. Once cap 360 is fully seated within retainer space 536, distal connecter 300 is able to rotate, but not move in an axial direction, relative to rear power housing 500, and ratchet coupler 400 may slide axially on mounting post 340 of tool connector 300 within cavity 540 of rear power housing 200. At this point, ratchet shifter 200, tool connector 300, ratchet coupler 400 and rear power housing 500 are assembled together for use with either optional handle grip 600 or a power instrument removably attachable to drive shaft 580 of rear power housing 500.

In operation, handle 1000 may be used as a ratchet drive in either a clockwise or counter-clockwise direction to, for example, screw or unscrew a fastener into or out of bone during, for example, an orthopedic extremity, large joint or spinal surgery. First, a screw or drill bit may be inserted through opening 232 of ratchet shifter and tool or instrument opening 330 of tool connector 300 into longitudinal bore 332 of tool connector 300 and removably coupled within by a coupling mechanism. If the surgeon or user desires to manually insert the screw, handle grip 600 is removably coupled to drive shank 580 of rear power housing 500 by inserting distal end 514 of drive shank 580 into longitudinal bore 630 at proximal end 612 of handle grip 600 until lip 654 of button 650 engages groove 572 of shank base 570 of rear power housing 500 or unless stopped by, for example, boss 560 or proximal end 612 of handle grip 612. If the surgeon or user desires to insert the screw using, for example, a power drill or instrument, drive shank 580 is removably attached to the coupling mechanism of the power drill or instrument. In accordance with one or more aspects of the present invention, handle 1000 is designed for a surgeon or user to easily transition between power and manual application of torque.

Handle 1000 allows ratcheting in both the clockwise or insertion direction and the counter-clockwise or withdrawal direction. For example, when ratchet shifter 200 is pulled axially away from tool connector 300, handle 1000 is in a status allowing clockwise screwing and counter-clockwise ratcheting while, for example, inserting a fastener into bone. This mode of operation is illustrated in FIGS. 8A-8C. When ratchet shifter 200 is pushed axially toward tool connector 300, handle 1000 is in a status allowing counter-clockwise withdraw of a fastener from bone and clockwise ratcheting. This mode of operation is illustrated in FIGS. 9A-9C. Both of these modes of operation will be described in more detail based on the embodiments described herein.

FIGS. 8A-8C illustrate a first mode of operation of handle 1000. In the first mode of operation that allows for clockwise screwing and counter-clockwise ratcheting, ratchet shifter 200 is pulled axially away from proximal end 312 of tool connector 300. As this happens, guide projections 234 slide within guide slots 370. At the same time, ratchet coupler 400 slides along mounting post 340 of tool connector 300 based on the movement of ratchet shifter 200 and attachment of clips 240 of ratchet shifter 200 in circumferential groove 402 of ratchet coupler 400. While this is happening, tool connector 300 and rear power housing 500 remain rotatably coupled and do not move axially relative to each other or relative to the movement of ratchet shifter 200 and ratchet coupler 400.

As ratchet coupler 400 slides on mounting post 340 as a result of pulling ratchet shifter 200 away from proximal end 312 of tool connector, ratchet coupler 400 moves towards proximal end 512 of rear power housing 500. In the first mode of operation, first forward portion 430 of ratchet coupler 400 aligns with forward circumferential surface 542 and second rear portion 460 aligns with neutral circumferential surface 544. In this configuration, as illustrated, for example, in FIG. 8C, fingers or hinges 440 on first forward portion 430 engage teeth 560 on forward circumferential surface 542 within cavity 540 of rear powering housing 500, and fingers or hinges 470 on second rear portion 460 do not engage any teeth. When fingers or hinges 440 engage with teeth 560, clockwise motion of drive shaft 580 of rear power housing 500 (e.g. by either manually by handle grip 600 or by a power instrument removably coupled to drive shaft 580) engages or digs distal ends 444 of fingers or hinges 440 into stop surfaces 564 of teeth 560, thus translating torque in a clockwise direction into the driven instrument (e.g drill or screwdriver bit) coupled in longitudinal bore 320 of tool connector 300. In one embodiment, inner surface 524 of side wall 522 may include some type of detent(s), catch or bump(s) (not shown) on or between one or more of forward circumferential surface 542, neutral circumferential surface 544 and/or rear circumferential surface 546 to retain ratchet coupler 400 in the first mode of operation and prevent ratchet coupler 400 from sliding on mounting post 340. In this example, the detent(s), catch or bump(s) may require some type of force or urging by a surgeon or user to shift between the first mode and the second mode of operation. Alternatively, the detent(s), catch or bump(s) may be included on mounting post 340 and/or on the inner surface of through—hole 422 of ratchet coupler 400.

Counterclockwise motion of drive shaft 580 allows fingers or hinges 440 to easily push past or pass over inclined surfaces 562 of teeth 560, resulting in a ratcheting or free rotation in the counterclockwise direction. In one example, a "clicking" sound may be heard each time a finger or hinge 440 passes over the apex of teeth 560. The more teeth there are, the less movement is needed on a return stroke.

When a change in ratcheting direction is required or desired, a second mode of operation may be engaged. The second mode of operation is illustrated in FIGS. 9A-9C. To engage the second mode of operation that allows for counter-clockwise withdraw of a fastener from bone and clockwise ratcheting, ratchet shifter 200 is pushed axially towards proximal end 312 of tool connector 300. As this happens, guide projections 234 are configured to slide within guide slots 370. At the same time, ratchet coupler 400 is configured to slide along mounting post 340 of tool connector 300 based on the movement of ratchet shifter 200 and attachment of clips 240 of ratchet shifter 200 in circumferential groove 402 of ratchet coupler 400. While this is happening, tool connector 300 and rear power housing 500 remain rotatably coupled and do not move axially relative to each other or relative to the movement of ratchet shifter 200 and ratchet coupler 400.

As ratchet coupler 400 slides on mounting post 340 as a result of pushing ratchet shifter 200 towards proximal end 312 of tool connector, ratchet coupler 400 moves away from proximal end and further into cavity 540 of rear power housing 500. In the second mode of operation, first forward portion 430 of ratchet coupler 400 aligns with neutral circumferential surface 544 and second rear portion 460 aligns with rear circumferential surface 546. In this configuration, as illustrated, for example, in FIG. 9C, fingers or hinges 440 on first forward portion 430 do not engage any teeth. In one embodiment, neutral circumferential surface 544 has second diameter 545 with no teeth to catch or grab fingers or hinges 440. In one example, second diameter 545 of neutral circumferential surface 544 is smaller than first diameter 543 of forward circumferential surface 542. In this example, neutral circumferential surface 544 may flex or push fingers or hinges 440 radially inward. However, since there are no teeth on neutral circumferential surface 544, fingers or hinges 440 may freely rotate in either a clockwise or counter-clockwise direction.

In the second mode of operation, fingers or hinges 470 on second rear portion 460 engage teeth 561 on rear circumferential surface 546 within cavity 540 of rear powering housing 500. When fingers or hinges 470 engage with teeth 561, counter-clockwise motion on drive shaft 580 of rear power housing 500 (e.g. by either manually by handle grip 600 or by a power instrument removably coupled to drive shaft 580) engages or digs distal ends 474 of fingers or hinges 470 into stop surfaces 565 of teeth 561, thus translating torque in a counter-clockwise direction into the driven instrument coupled to longitudinal bore 320 of tool connector 300.

Clockwise motion of drive shaft 580 allows fingers or hinges 470 to easily push past or pass over inclined surfaces 563 of teeth 561, resulting in a ratcheting or free rotation in the counterclockwise direction. In one example, a "clicking" sound may be heard each time a finger or hinge 470 passes over the apex of teeth 561. The more teeth there are, the less movement is needed on a return stroke.

Ratchet shifter 200, tool connector 300, ratchet coupler 400, rear power housing 500 and optional handle grip 600 may all be manufactured by, for example injection molding, additive manufacturing or 3D printing. Also, each of these components may be cannulated along the longitudinal axis to permit passage of, for example, guidewires or K-wire, therethrough.

In one embodiment, ratchet shifter 200 may include a cut out 204, as shown in FIG. 2A, to accommodate a button or locking mechanism, which may be a part of tool connector 300, releasably engagable with a tool or instrument inserted in longitudinal bore 332 of tool connector 300.

While several aspects of the present invention have been described and depicted herein, alternative aspects may be effected by those skilled in the art to accomplish the same objectives. Accordingly, it is intended by the appended claims to cover all such alternative aspects as fall within the true spirit and scope of the invention.

The invention claimed is:

1. An apparatus for releasably holding a surgical tool, said apparatus comprising:
   a ratchet shifter, said ratchet shifter including a proximal end, a distal end and a body defining a through-hole;
   a tool connector, said tool connector including a longitudinal axis, a proximal end and a distal end, said tool connector further including a tool engagement body extending from the proximal end and a mounting post extending longitudinally along the longitudinal axis from the tool engagement body to the distal end, the tool engagement body including a tool engagement opening at the proximal end communicating with a longitudinal bore extending through at least a portion of the tool engagement body along the longitudinal axis, the longitudinal bore configured to releasably couple the surgical tool, said ratchet shifter telescopically receiving said tool connector and slidably moveable between a first position and a second position;
   a ratchet coupler, said ratchet coupler including a body defining a through-hole and an outer surface, the mounting post of said tool connector passing through the through hole of a cylindrical body, the mounting post slidably coupled to said ratchet coupler, the distal end of said ratchet shifter coupled to said ratchet coupler, the outer surface of said ratchet coupler including a first forward portion and a second rear portion, the first forward portion including a plurality of fingers extending radially outward from the outer surface, the second rear portion including a plurality of fingers extending radially outward from the outer surface;
   a rear power housing, said rear power housing rotatably coupled to the mounting post of said tool connector at the distal end, said rear power housing including a longitudinal axis, a body and a drive shaft extending longitudinally along the longitudinal axis from the body, the body including a cavity defining an inner surface, the inner surface comprising a forward circumferential surface, a neutral circumferential surface and a rear circumferential surface, the forward circumferential surface including a plurality of teeth projecting radially inward from the inner surface, the rear circumferential surface including a plurality of teeth projecting radially inward from the inner surface, wherein, in the first position, the plurality of fingers of the first forward portion of said ratchet coupler engage the plurality of teeth on the forward circumferential surface to allow ratcheting in a first direction and maximum torque in a second direction and the plurality of teeth of the second rear portion engage the neutral circumferential surface, wherein, in the second position, the plurality of fingers of the second rear portion of said ratchet coupler engage the plurality of teeth on the rear circumferential surface to allow ratcheting in the second direction and maximum torque in the first direction and the plurality of teeth of the first forward portion engage the neutral circumferential surface.

2. The apparatus for releasably holding a surgical tool of claim 1, wherein the drive shaft is removeably attachable to a handle grip.

3. The apparatus of claim 2, wherein said handle grip comprises a body, the body including a longitudinal axis and a longitudinal bore disposed along the longitudinal axis of the body, the longitudinal bore open at one end and configured to receive and removeably said rear power housing.

4. The apparatus of claim 3, wherein said rear power housing is removeably coupled within the longitudinal bore by a living hinge.

5. The apparatus of claim 2, wherein said handle grip comprises a body, the body in a shape apportioned to be grasped by a human hand.

6. The apparatus of claim 2, wherein said handle grip comprises a body, at least a portion of the body in a shape of a T-handle.

7. The apparatus of claim 2, wherein said handle grip comprises a body, at least a portion of the body in a shape of a pistol grip.

8. The apparatus of claim 2, wherein said handle grip comprises a body, at least a portion of the body in a shape of a palm handle.

9. The apparatus of claim 2, wherein said handle grip comprises a body, at least a portion of the body in a shape of a ball.

10. The apparatus of claim 1, wherein the drive shaft is removeably attachable to a power instrument.

\* \* \* \* \*

UNITED STATES PATENT AND TRADEMARK OFFICE
CERTIFICATE OF CORRECTION

PATENT NO.        : 12,023,014 B2
APPLICATION NO.   : 17/210609
DATED             : July 2, 2024
INVENTOR(S)       : Denham et al.

It is certified that error appears in the above-identified patent and that said Letters Patent is hereby corrected as shown below:

On the Title Page

Item (73)
Delete "NEXTREMITY SOLUTIONS, INC." and insert -- MEDARTIS AG --

Signed and Sealed this
First Day of April, 2025

Coke Morgan Stewart
*Acting Director of the United States Patent and Trademark Office*